United States Patent [19]
Ishikawa et al.

[11] Patent Number: 5,522,388
[45] Date of Patent: Jun. 4, 1996

[54] PULSE SPECTROMETER

[75] Inventors: Muneharu Ishikawa; Koji Katayama, both of Tsukuba, Japan

[73] Assignee: Kowa Company Ltd., Japan

[21] Appl. No.: 306,412

[22] Filed: Sep. 15, 1994

[30]   Foreign Application Priority Data

Sep. 22, 1993 [JP] Japan .................................. 5-235327

[51] Int. Cl.$^6$ ........................................................ A61B 5/00
[52] U.S. Cl. ............................................. 125/633; 356/39
[58] Field of Search ............................... 128/633, 664, 128/666, 667; 356/39, 40, 41

[56]   References Cited

U.S. PATENT DOCUMENTS

| | | | |
|---|---|---|---|
| 4,869,261 | 9/1989 | Penáz | 128/667 |
| 4,883,353 | 11/1989 | Hausman et al. | 128/633 |
| 4,927,264 | 5/1990 | Shiga et al. | 356/41 |
| 5,111,817 | 5/1992 | Clark et al. | 128/664 |
| 5,313,941 | 5/1994 | Braig et al. | 128/633 |
| 5,372,135 | 12/1994 | Mendelson et al. | 128/666 |

*Primary Examiner*—Angela D. Sykes
*Assistant Examiner*—Eric F. Winakur
*Attorney, Agent, or Firm*—Adams & Wilks

[57]   ABSTRACT

A pulse spectrometer for noninvasively determining the concentration of blood constituents in in vivo tissue comprises a pressure application device for applying pressure to a measurement region of the in vivo tissue and a light source for irradiating the measurement region of the in vivo tissue with light. A spectroscope separates light transmitted from the measuring region into its spectral components, and a first light-receiving element receives the spectral components. A second light-receiving element receives scattered light from a vicinity of the measurement region. A control device controls the pressure which is applied on the measurement region by the pressure application device based on a signal obtained from the second light-receiving element. A signal separator separates a blood flow variation component from the spectral components received by the first light-receiving element based on the signal from the second light-receiving element.

12 Claims, 5 Drawing Sheets

PULSE SPECTROMETER

BACKGROUND OF THE INVENTION

1. Field of the Invention

The present invention relates to a pulse spectrometer, and particularly to a pulse spectrometer which irradiates the measurement region of an in vivo tissue with light and conducts spectroscopic analysis for noninvasively determining the concentration of blood constituents.

2. Description of the Prior Art

In conventional noninvasive measurement of in vivo tissue blood constituents by near infrared spectrometry the measured value tends to fluctuate with the amplitude of the pulsation at the measurement region. The measurement therefore has to be conducted over a long period for averaging out the effects of the pulsation.

When in vivo tissue is irradiated with light, the transmission of the light through the tissue is accompanied by light absorption by the blood and light absorption by the tissue. In noninvasive measurement of blood component concentration, the measurement accuracy is degraded by the tissue light absorption.

Water has a particularly large effect on measurement accuracy because it makes up 50–60% of body tissue and has a major absorption peak at wavelengths in the vicinity of 980 nm, which is the wavelength region in which the absorption peaks of most of the blood constituents to be measured fall.

These circumstances make it necessary to eliminate the effect of the tissue so as to increase the relative amount of light absorbed by the blood constituents. For eliminating the effect of the tissue, it is advantageous to extract the amount of change in light absorbance of the blood caused by pulsation. Moreover, the fact that concentration measurement requires an absolute quantity of blood makes it essential to measure the amount of absorbance.

The pulse oximeter was developed on the basis of this knowledge to positively utilize blood pulsation for obtaining spectroscopic information from blood in an in vivo tissue. The pulse oximeter measures the oxygen saturation degree of blood hemoglobin by using the change in absorbance caused by pulsation as a signal source and measuring the amount of change at each of two wavelengths during each segment of a subdivided pulse period. Since this method can determine the oxygen saturation degree by a comparison between two frequencies, the calculation uses only the change in the amount of absorption by the blood.

As this signal processing method ignores the total amount of absorption, however, it cannot measure the hemoglobin concentration of the blood and other such concentrations that relate to the absolute value of the light absorbance. It is therefore not appropriate for analyzing blood component concentration.

Japanese Patent Laid-open Publication No. Hei 4(1982)-60650 teaches another device that utilizes pulsation by using a blood pressure and blood oxygen saturation degree measurement technique based on what is known as the volumetric vibration method. This device applies cuff pressure to the measurement region for reading the light absorbances of the tissue, vein and artery layers in various combinations and then calculates the oxygen saturation degrees of the arterial blood and veinal blood by determining the difference in light absorbance of the combinations at two wavelengths, and further measures the blood pressure from the cuff pressure at the change points of the pulse amplitude.

Regarding the application of cuff pressure, Japanese Patent Laid-open Publication No. Hei 5(1993)-503856 teaches a method of determining arterial blood oxygen saturation degree and arterial blood pressure in which the light absorbance of the arterial blood is measured under a cuff pressure approximately equal to the arterial pressure so as ascertain the change in light absorbance with pulsation at maximum amplitude.

The prior art devices for analyzing in vivo tissue blood constituents by near infrared spectrometry utilize only measured change in the arterial signal and difference in light absorbance. As a result, they are capable of determining only the blood oxygen saturation degree and do not employ any means or method for utilizing the light absorbance value or other blood component concentration data.

SUMMARY OF THE INVENTION

An object of this invention is to overcome the foregoing drawbacks of the prior art by providing a pulse spectrometer capable of accurately measuring light absorbance data related to blood constituents and using the measured data for analyzing blood component concentration.

In accordance with the invention, the above object is achieved by a pulse spectrometer which noninvasively determines the concentration of blood constituents in in vivo tissue by irradiating a measurement region of the in vivo tissue with light and spectroscopically analyzing light from the in vivo tissue. The pulse spectrometer comprises a light source for irradiating an in vivo tissue measurement region with light, fixing means for fixing the measurement region by applying pressure thereon, spectroscopic means for separating light from the measurement region into its spectral components, a first light-receiving element for receiving the spectrally separated light, a second light-receiving element for receiving scattered light from the vicinity of the measurement region, means for optimally controlling the pressure applied by the fixing means based on a signal obtained from the second light-receiving element, and signal component separation means for, based on the signal from the second light-receiving element, separating out only the blood flow variation component from among the components of the signal from the first light-receiving element.

In this arrangement, the separation of only the blood flow variation component from among the components of the signal from the first light-receiving element based on the signal obtained from the second light-receiving element makes it possible to measure signals corresponding to the systole and diastole that occur synchronously with the pulsation-induced variation in blood quantity, extract only data relating to the blood from the in vivo tissue data, and quantitatively determine various blood component quantities from the shape of the light spectrum. Moreover, by determining the difference in spectrum between the systole and diastole it becomes possible to directly calculate the light absorbance spectrum of the blood without need for a reference light for light source spectrum correction.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENT

Figure 1:
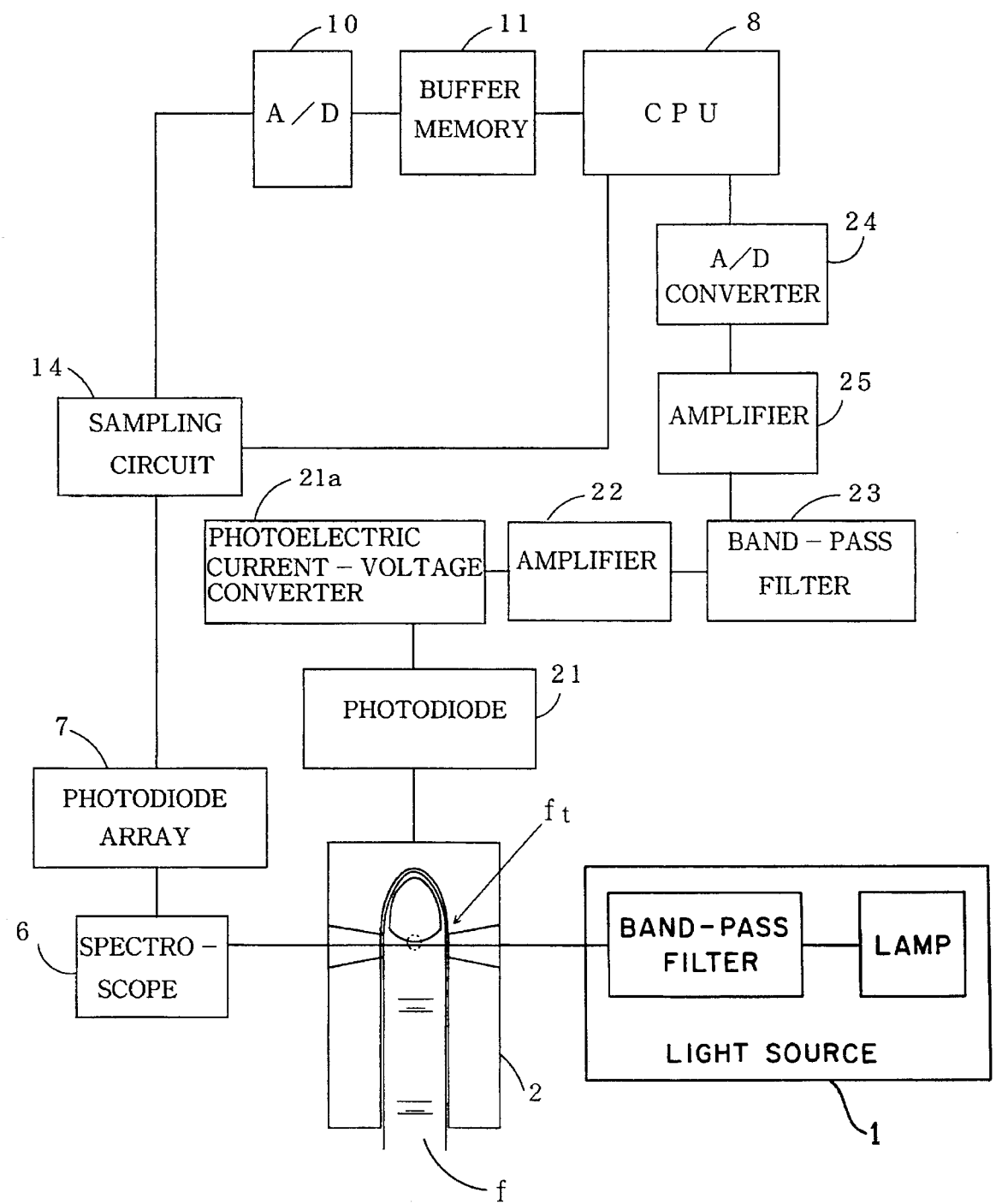
FIG. 1 is a block diagram for illustrating the arrangement of a pulse spectrometer of the invention.

The invention will now be described in detail on the basis of the preferred embodiment illustrated in the drawings. The embodiment described in the following is an application of the invention to the measurement of a light spectrum carrying information regarding the component concentration of blood in a human finger.

A block diagram of the pulse spectrometer according to the invention is shown in FIG. 1. The pulse spectrometer has a light source 1 comprising a halogen lamp, a power supply for driving the light source 1, a mirror for selectively reflecting near infrared light of a wavelength of 600–1100 nm, and a condenser lens for converging light on a measurement region. The mirror provided in the light source 1 is for protecting the measurement region from being burned by heat waves emitted by the halogen lamp and for removing stray light in the spectroscope. It is possible to replace the mirror with one or more filters arranged to selectively transmit the same wavelength band. (The wavelength band is not limited to that mentioned above and can be changed as desired in accordance with the absorption wavelengths of the blood constituents to be measured.)

The subject to be tested inserts his or her finger f upward (as seen in FIG. 1) into a probe 2 having windows for light passage on the left, right and bottom. The finger tip (the measurement region) ft is positioned at the windows. The fixing of the finger f by the probe and the detection of pulses will be explained later.

Light emitted by the light source 1 and entering the probe 2 from the right side in FIG. 1 irradiates the measurement region ft, passes through the finger tissue, exits the left side of the probe 2 and enters a spectroscope 6.

The spectroscope 6, which is a monochromator comprising a diffraction grating and a convex mirror, spectrally separates the light passing through the measurement region into individual wavelengths in the 600–1100 nm wavelength range. The light spectrum is detected by a photodiode array 7 and, under the control of a CPU (central processing unit) 8, is sampled by a sampling circuit 14, is converted to a digital signal by an A/D converter 10, and is stored in a buffer memory 11. The CPU 8 issues commands for sequentially reading the data stored in the buffer memory 11.

Figure 2:
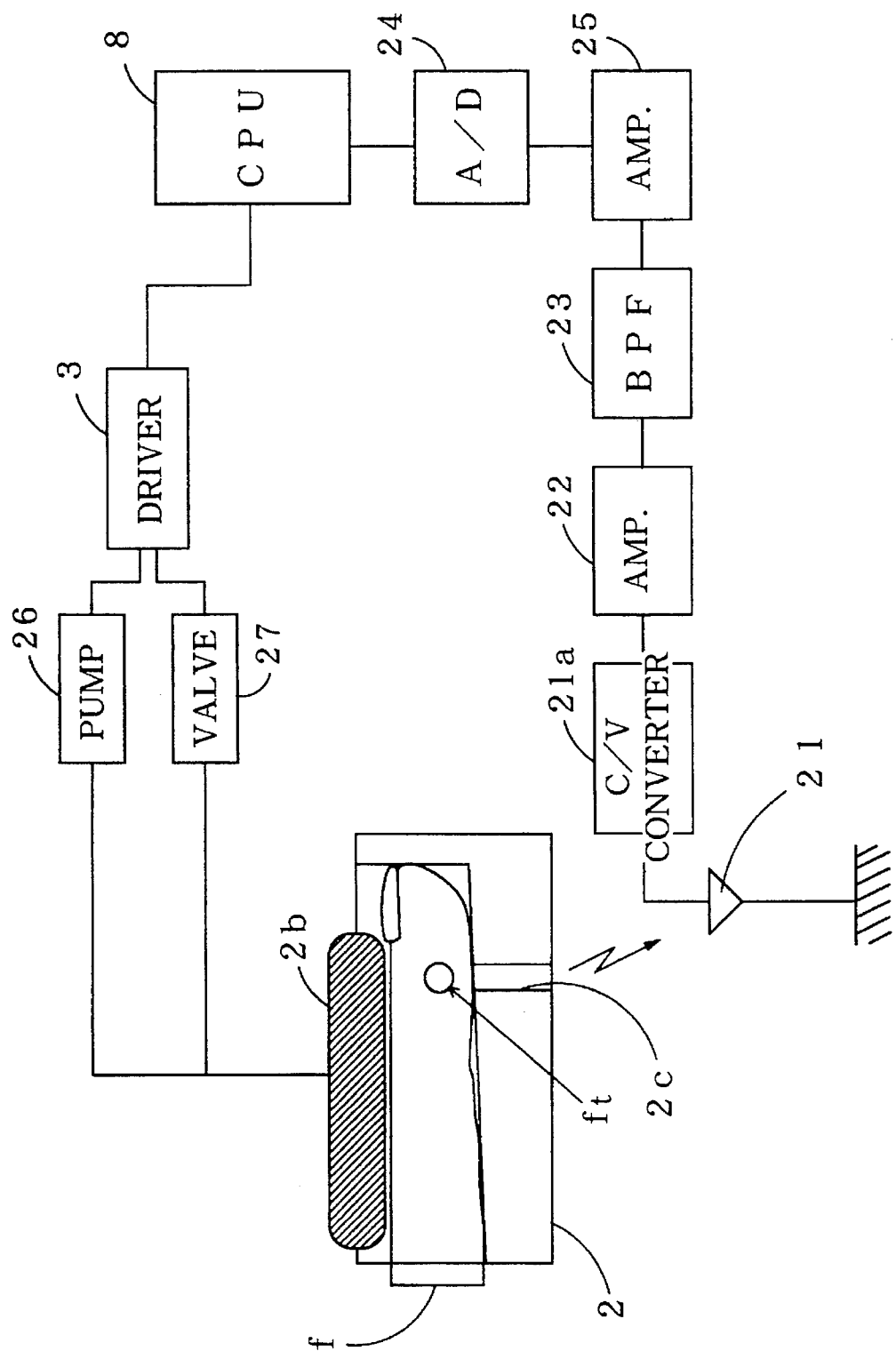
FIG. 2 is a block diagram showing the arrangement of a pulse detection means of the pulse spectrometer of FIG. 1.

The structure of the probe 2 and the arrangement of the pulse detection means are shown in the block diagram of Figure 2. Light scattered within the tissue and passing through a window 2c at the bottom of the probe 2 (under the finger tip ft) is detected by a photodiode 21 for use in pulse monitoring.

The photoelectric current output by the photodiode 21 is converted to voltage by a photoelectric current-voltage converter 21a, amplified by an amplifier 22, passed through a band-pass filter 23 for removing the signal dc component and high-frequency noise, amplified by an amplifier 25, converted to a digital signal by an A/D converter 24, and input to the CPU 8. The band-pass filter 23 is used for removing the dc component of the signal so as to enable pulse extraction and for removing power source noise and other high-frequency noise components.

As it monitors the pulses detected via the photodiode 21, the CPU 8 determines the maximum and minimum values during each pulse cycle and synchronously with the occurrence of each of the values sends a signal to the sampling circuit 14 for sampling a signal from the photodiode array 7.

Furthermore, as it monitors the pulses, the CPU 8 prevents the pulse amplitude from falling to zero by controlling a pump 26 and a solenoid valve 27 through a drive circuit 3 so as to regulate the pressure in a balloon 2b. The regulated pressure value is maintained throughout the measurement for fixing the finger f.

The pressure of the balloon 2b is set to the optimum value for stabilizing the finger without hindering the flow of arterial or veinal blood at the measurement region and for stabilizing the pulse amplitude over time. Although the present embodiment assumes the pressure value to be 20 mm Hg, this is not limiting and the pressure is regulated to the optimum value for each measurement.

As will be understood from the foregoing, in the illustrated embodiment, the measurement region is fixed by the balloon during signal integration and the balloon pressure is controlled for obtaining constant pulse amplitude.

Although the finger tissue transmits light of wavelengths in the near infrared band to some degree, a large part of the light is scattered during passage. As a result, the light directed onto the measurement region disperses equally in all directions from the point of incidence, so that light leaves the finger similarly in all directions. In addition, the amount of light leaving the tissue varies as the amount of light absorbed by the blood changes with the variation in the amount of blood present in the tissue at the measurement region that is caused by the pulsation of the heart.

As the light transmitting through the measurement region is being picked up by the spectroscope 6, the photodiode 21 simultaneously picks up light from another direction for measuring the change in blood quantity due to heart pulsation and the signal is processed synchronously with the pulsation. Specifically, as will be explained in more detail later, the maximum and minimum values of the intensity of the light received by the spectroscope 6 during a single pulse cycle are detected and the light spectrum is produced at the time of each detected value.

For enhancing the accuracy of the measurement by this method, it is important for the pulses to be detected at a steady and strong amplitude. Although the earlier mentioned Japanese Patent Laid-open Publication No. Hei 5(1993)-503856 teaches that pulse strength can be effectively increased by applying a cuff pressure substantially equal to the arterial pressure, for realizing the purpose of the present invention it is even more important for the pulses to be steady, the measurement region to be fixed and the length of the optical path to be constant.

Figure 5:
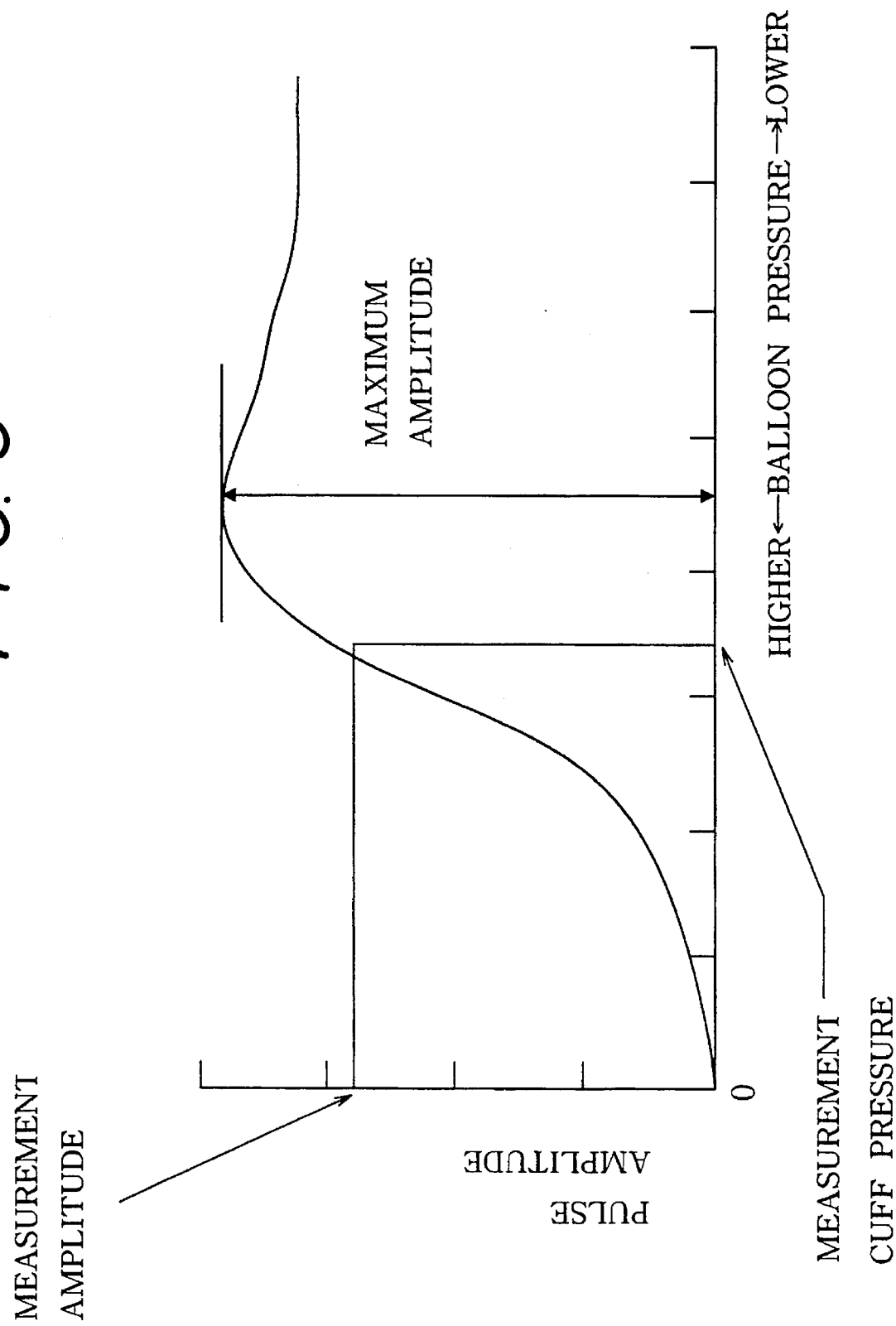
FIG. 5 is a graph showing how pulse amplitude varies with cuff pressure.

In this invention, therefore, the approach adopted for fixing the measurement region and stabilizing the pulse amplitude is to facilitate pulse amplitude control not by use of a cuff pressure equal to the arterial pressure but by use of a cuff pressure at a point that is linearly correlated with the pulse amplitude. Thus, it was found that measurement is preferably conducted while, as shown in FIG. 5, the cuff pressure is controlled not at a point at which the pulse amplitude becomes maximum, but at a region at which the linearity between the cuff pressure and the pulse amplitude is maintained, that is, at which the amplitude becomes about ⅔ of the maximum amplitude.

Figure 3:
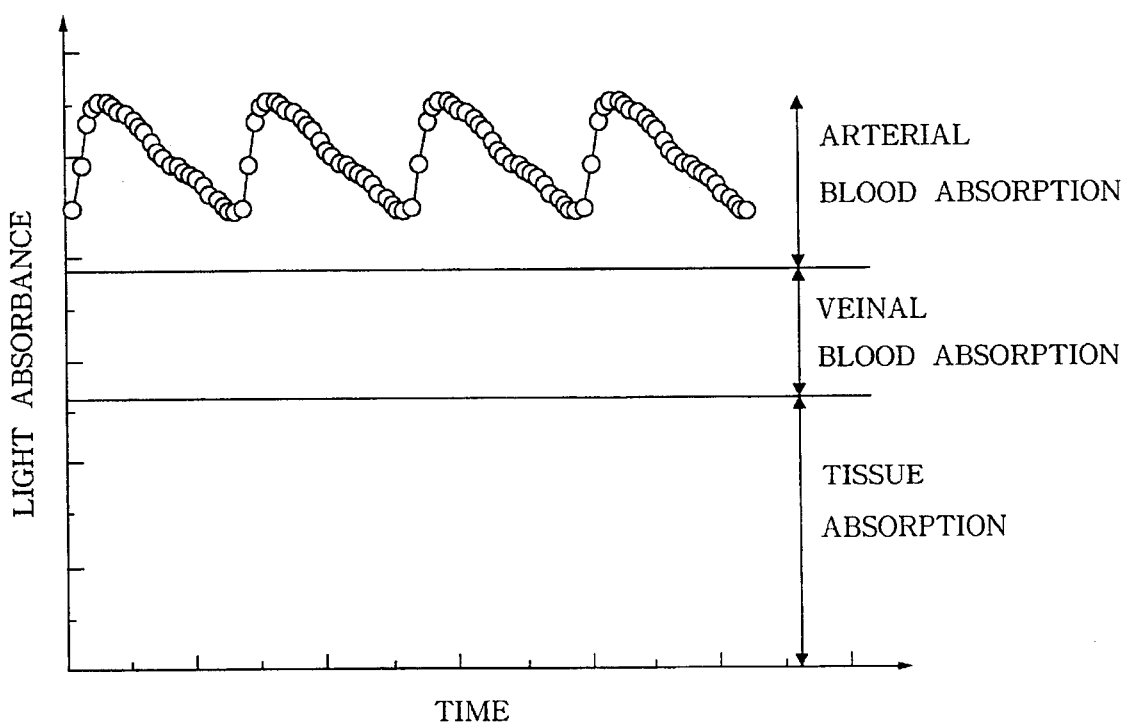
FIG. 3 is a graph showing the time-course fluctuation of the logarithmically converted value of a signal obtained from light transmitted through in vivo tissue.

FIG. 3 shows the pulse component measured in this state as expressed in terms of light absorbance. The absorption by the in vivo measurement subject is attributable to that by the tissue, that by arterial blood and that by veinal blood. Since the absorptions by the tissue and the veinal blood are affected only slightly by the pulsation, they are steady over time. On the other hand, the absorption by the arterial blood varies greatly with pulsation and, as can be seen in FIG. 3, fluctuates periodically. What is required is the concentration of the blood constituents, particularly the concentration of the physiologically important arterial blood constituents.

It is therefore necessary to ascertain the absorption by the arterial blood only, independently of the effects of the tissue and veinal blood. The method used for this purpose by the illustrated embodiment is to determine the difference between the maximum and minimum values of the light absorbance spectrum synchronously with the pulses detected via the photodiode 21. Since the change in light absorbance with pulsation reflects the rise and fall in the amount of arterial blood, the method of determining the difference between the maximum and minimum values synchronously with the pulsation is an effective way of extracting information relating solely to the arterial blood.

Specifically, the analysis is conducted by subjecting the minimum and maximum value signals to divisional operation and logarithmic conversion at each wavelength. If required, moreover, the accuracy is enhanced by integrating the division-subjected signals over multiple periods.

When, as in this invention, a method for determining the difference spectrum is adopted, the measurement can be conducted without need for the reference light required by ordinary spectroscopes. More specifically, defining the light source spectrum as $I0(\lambda)$ and the spectrum at the maximum pulse value as $Imax(\lambda)$, the light absorbance Abs max can be expressed as $$Abs\ max = -\log(Imax(\lambda)/I0(\lambda)) \quad (1)$$

Similarly, defining the spectrum at the minimum pulse value as $Imin(\lambda)$, it follows that $$Abs\ min = -\log(Imin(\lambda)/I0(\lambda)) \quad (2)$$

Therefore, since the difference spectrum (1)–(2) is $$Abs\ max - Abs\ min = -\log(Imax(\lambda)/Imin(\lambda)) \quad (3)$$

the light absorbance can be obtained without measurement of a reference light.

Figure 4:
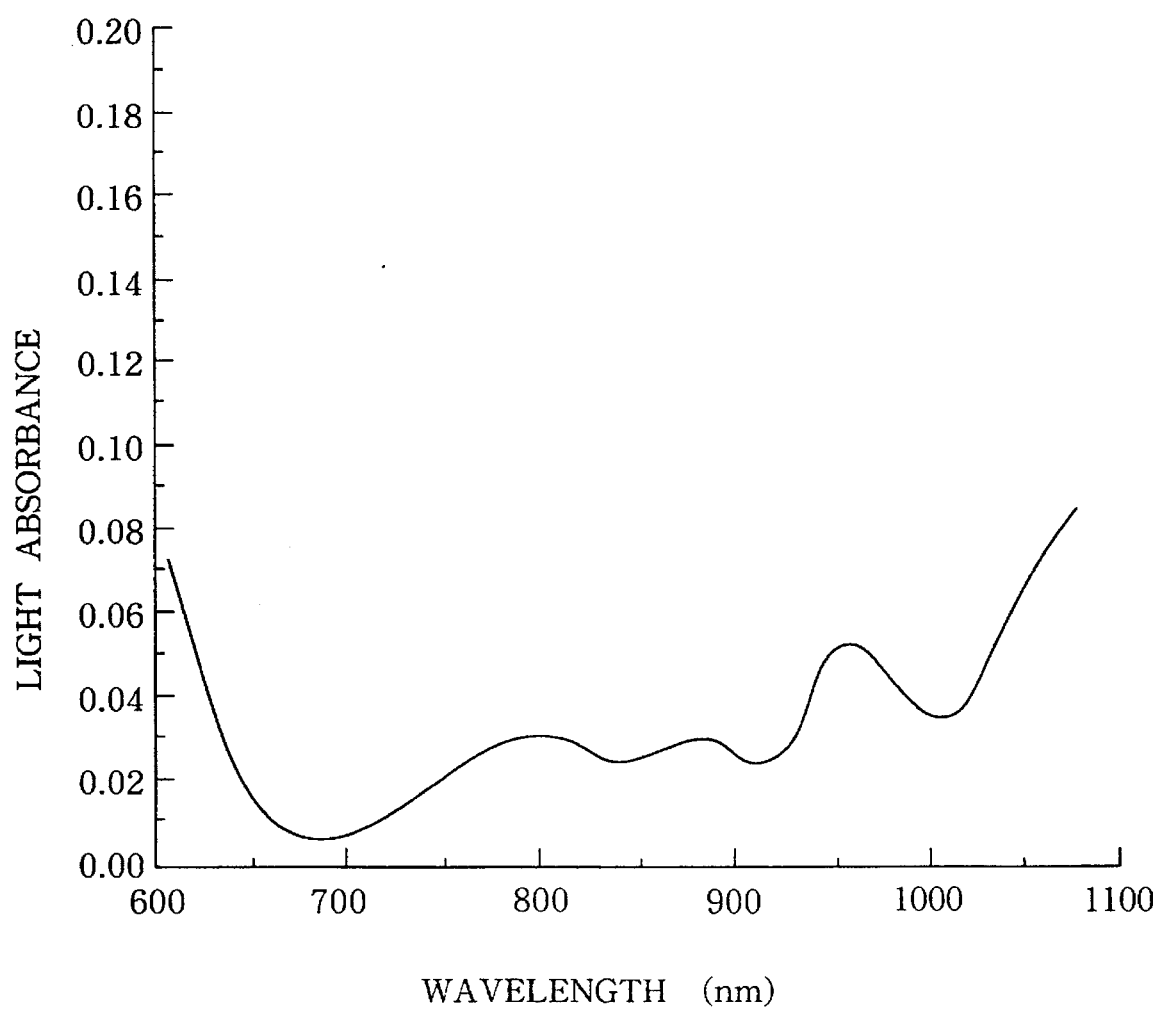
FIG. 4 is a graph showing a blood component absorption spectrum measured by an embodiment of the invention.

FIG. 4 shows light absorbance spectral data measured by the invention. The spectral data of this figure was obtained by sampling the outputs of the photodiode array 7 at a sampling interval of 100 ms, dividing the spectrum at the maximum value by the spectrum at the minimum value in one cycle of pulse, integrating the divisional values over multiple cycles, and subjecting them to logarithmic conversion in the CPU 8, thus defining the light absorbance. In the illustrated embodiment data consistency is enhanced by integration over 100 cycles. The number of integration cycles does not necessarily have to be 100, however, but can be selected as desired in view of the light quantity and the required measurement accuracy.

This invention does not particularly specify the measurement region. While the illustrated embodiment uses a finger as the measurement region, it is alternatively possible to use the ear lobe or any other portion of the body which permits detection of light passing therethrough.

Being equipped with a measurement region fixing means and a pulse detection means, the embodiment described in the foregoing detects a pulse signal from the measurement region, detects the maximum and minimum values of the pulse signal during each cycle thereof, and based on the so-obtained information determines the difference between the spectra of the light passing through the measurement region. Owing to this arrangement, the pulse spectrometer is able to eliminate information related to the tissue of the measurement region, extract only information related to the blood at the measurement region, and quantitatively determine various blood component quantities from the shape of the light spectrum. Moreover, by determining the difference spectrum between the systole and diastole it becomes possible to directly calculate the light absorbance spectrum of the blood without need for a reference light for light source spectrum correction.

In addition, since fluctuation in the transmitted light quantity is suppressed by regulating the fixing pressure for the measurement region synchronously with the detected pulsation, the absorption spectrum produced by the blood constituents can be independently extracted. This is particularly advantageous in the case of measuring glucose and other blood constituents that produce minute signals since it enables the accuracy of the measurement to be enhanced by minimizing the effect of water. The measured spectral data can thus be used for noninvasively determining not only the oxygen saturation degree but also various components contained in the blood.

As set out in the foregoing, the invention provides a high-performance pulse spectrometer which noninvasively determines the concentration of blood constituents in in vivo tissue by irradiating a measurement region of the in vivo tissue with light and spectroscopically analyzing light from the in vivo tissue. For this, the pulse spectrometer according to the invention comprises a light source for irradiating an in vivo tissue measurement region with light, fixing means for fixing the measurement region by applying pressure thereon, spectroscopic means for separating light from the measurement region into its spectral components, a first light-receiving element for detecting the spectrally separated light, a second light-receiving element for detecting scattered light from the vicinity of the measurement region, means for optimally controlling the pressure applied by the fixing means based on a signal obtained from the second light-receiving element, and signal component separation means for, based on the signal from the second light-receiving element, separating out only the blood flow variation component from among the components of the signal from the first light-receiving element.

Thus, since the pulse spectrometer is able to separate the blood flow variation component from among the components of the signal from the first light-receiving element based on the signal obtained from the second light-receiving element, it is able to measure signals corresponding to the systole and diastole occurring synchronously with the pulsation-induced variation in blood quantity, independently extract only data relating to the blood from the in vivo tissue data, and quantitatively determine various blood component quantities from the shape of the light spectrum. Moreover, by determining the difference spectrum between the systole and diastole, the pulse spectrometer is able to directly calculate the light absorbance spectrum of the blood without need for a reference light for light source spectrum correction.

What is claimed is:

1. A pulse spectrometer for noninvasively determining the concentration of blood constituents in in vivo tissue by irradiating a measurement region of the in vivo tissue with light and spectroscopically analyzing light from the in vivo tissue, the pulse spectrometer comprising:

light source means for irradiating an in vivo tissue measurement region with light;

fixing means for fixing the measurement region by application of a pressure thereon;

spectroscopic means for separating light transmitted from the measurement region into its spectral components;

a first light-receiving means for receiving the separated light spectral components;

a second light-receiving means for receiving scattered light from a vicinity of the measurement region and generating a signal based on a quantity of light received;

means for optimally controlling the pressure applied on the measurement region by the fixing means based on the signal obtained from the second light-receiving means; and signal component separation means for, based on the signal from the second light-receiving means, separating out only a blood flow variation component from among the spectral components received by the first light-receiving means.

2. A pulse spectrometer according to claim 1; wherein the light source means comprises a lamp for producing a continuous spectrum and a band-pass filter for selectively irradiating the in vivo tissue only with light from the continuous spectrum falling in a wavelength range of 600–1100 nm.

3. A pulse spectrometer according to claim 1; wherein the signal component separation means separates the blood flow variation component from the spectral components received by the first light-receiving means synchronously with variation in the quantity of the scattered light received by the second light-receiving means.

4. A pulse spectrometer according to claim 1; wherein the fixing means comprises a balloon having an air pressure for applying a pressure to the measurement region of the in vivo tissue, the means for controlling the pressure applied by the balloon regulating the air pressure of the balloon to an optimum value within a range within which a variation in the quantity of the scattered light received by the second light-receiving means is present.

5. A pulse spectrometer according to claim 4; wherein the means for optimally controlling the pressure applied on the measurement region comprises a pump connected to the balloon, and control means for controlling the operation of the pump to regulate the air pressure in the balloon.

6. A pulse spectrometer for noninvasively determining the concentration of blood constituents in in vivo tissue, the pulse spectrometer comprising:

pressure applying means for applying a pressure to a measuring region of an in vivo tissue;

light source means for illuminating the measuring region with light;

spectroscopic means for separating light transmitted from the measuring region into its spectral components;

first photodetecting means for detecting the spectral components of the light transmitted from the measuring region;

second photodetecting means for detecting scattered light from a vicinity of the measuring region and generating a signal based on a quantity of light detected;

control means for controlling the pressure applying means based on the signal obtained from the second photodetecting means; and signal separation means for separating a blood flow variation component from the spectral components detected by the first photodetecting means based on the signal obtained from the second photodetecting means.

7. A pulse spectrometer according to claim 6; wherein the light source means includes means for producing a continuous spectrum, and filter means for selectively illuminating the in vivo tissue only with light from the continuous spectrum.

8. A pulse spectrometer according to claim 7; wherein the continuous spectrum is within a wavelength range of 600–1100 nm.

9. A pulse spectrometer according to claim 8; wherein the means for producing a continuous spectrum comprises a lamp, and the filter means comprises a band-pass filter.

10. A pulse spectrometer according to claim 6; wherein the signal separation means separates the blood flow variation component from the spectral components detected by the first photodetecting means synchronously with variation in the quantity of the scattered light received by the second photodetecting means.

11. A pulse spectrometer according to claim 6; wherein the pressure applying means comprises a balloon having an air pressure for applying the pressure to the measurement region of the in vivo tissue, the control means regulating the air pressure of the balloon to an optimum value within a range within which a variation in the quantity of the scattered light received by the second photodetecting means is present.

12. A pulse spectrometer as claimed in claim 11; wherein the control means comprises a pump connected to the balloon, and driving means for controlling the operation of the pump to regulate the air pressure in the balloon.

* * * * *